(12) United States Patent
Manigel et al.

(10) Patent No.: US 9,744,299 B2
(45) Date of Patent: Aug. 29, 2017

(54) DATA PROCESSING DEVICE FOR AN ANESTHESIA DEVICE

(71) Applicants: Dräger Medical GmbH, Lübeck (DE); Inselspital-Stiftung Bern, Bern (CH)

(72) Inventors: Jürgen Manigel, Klingberg (DE); Martin Luginbühl, Hinterkappelen (CH)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 626 days.

(21) Appl. No.: 13/894,655

(22) Filed: May 15, 2013

(65) Prior Publication Data

US 2013/0306063 A1 Nov. 21, 2013

(30) Foreign Application Priority Data

May 15, 2012 (DE) .................. 10 2012 009 617

(51) Int. Cl.
*A61M 5/168* (2006.01)
*A61M 16/10* (2006.01)
(Continued)

(52) U.S. Cl.
CPC ...... *A61M 5/16886* (2013.01); *A61M 16/104* (2013.01); *A61M 16/18* (2013.01);
(Continued)

(58) Field of Classification Search
CPC ............. A61M 5/16886; A61M 16/01; A61M 16/104; A61M 16/18; A61M 2230/432;
(Continued)

(56) References Cited

U.S. PATENT DOCUMENTS 7,556,036 B2 * 7/2009 Bouillon ............... A61M 16/18
128/200.24
7,878,982 B2 * 2/2011 Frank .................. A61B 5/0205
600/301
(Continued)

FOREIGN PATENT DOCUMENTS

CN 1780605 A 5/2006
CN 101472631 A 7/2009
(Continued)

OTHER PUBLICATIONS

T. Bouillon et al., Anesthesiology, 2004; 100; 1353-1372.

*Primary Examiner* — Lynne Anderson
*Assistant Examiner* — Elliot S Ruddie
(74) *Attorney, Agent, or Firm* — McGlew and Tuttle, P.C.

(57) ABSTRACT

A data processing device is provided for an anesthesia device for feeding an intravenously administered hypnotic, a volatile hypnotic, and an opioid such that the volume flow can be adjusted. The device determines and standardizes the effective concentrations of the anesthetics. A pharmacokinetic model adds up the standardized concentrations of the hypnotics to a total hypnotic concentration. An isobole is calculated based on a coordinate plane with a total hypnotic concentration axis and an opioid concentration axis, as a function of the currently determined concentrations. The system displays a two-dimensional action diagram with the y-axis as an indicator of the total hypnotic concentration and the x-axis as an indicator of the standardized opioid concentration. The calculated standardized total hypnotic concentration and opioid concentration and the isoboles determined are displayed. The display is adapted to changes occurring in the isoboles determined in the course of time.

18 Claims, 5 Drawing Sheets

(51) Int. Cl.
   *A61M 16/18* (2006.01)
   *G06F 19/00* (2011.01)
(52) U.S. Cl.
   CPC .......... *A61M 2016/1035* (2013.01); *A61M 2205/502* (2013.01); *G06F 19/3456* (2013.01)
(58) Field of Classification Search
   CPC .... A61M 2016/1035; A61M 2205/502; A61M 2005/14296; A61M 2230/06; A61M 2230/205; A61M 2230/30; G06F 19/3456; A61B 5/0205; A61B 5/024; A61B 5/0836; A61B 5/4821
   USPC ............ 702/19; 128/200.24, 203.12, 203.13, 128/203.14, 203.15, 203.22, 204.12, 128/204.21, 204.23; 600/301, 310–314, 600/486; 604/503, 504, 512
   See application file for complete search history.

(56) References Cited

U.S. PATENT DOCUMENTS

| | | |
|---|---|---|
| 2006/0081244 A1 | 4/2006 | Bouillon et al. |
| 2008/0234322 A1 | 9/2008 | Syroid et al. |
| 2011/0105914 A1 | 5/2011 | Frank et al. |

FOREIGN PATENT DOCUMENTS

| | | |
|---|---|---|
| DE | 10 2004 050 717 B3 | 9/2005 |
| DE | 10 2007 038 975 A1 | 1/2009 |
| EP | 2194474 A1 | 6/2010 |

\* cited by examiner

DATA PROCESSING DEVICE FOR AN ANESTHESIA DEVICE

CROSS REFERENCE TO RELATED APPLICATIONS

This application claims the benefit of priority under 35 U.S.C. §119 of German Patent Application DE 10 2012 009 617.8 filed May 15, 2012, the entire contents of which are incorporated herein by reference.

FIELD OF THE INVENTION

The present invention pertains to a data processing device or data processing system for an anesthesia device with means for feeding three anesthetics, namely, two hypnotics, one of them being an intravenously administered hypnotic and the other being a volatile hypnotic, and an opioid, wherein such feeding is controlled such that the volume flow can be adjusted, wherein the data processing device is set up (configured) to receive data on the anesthetic volume flows being fed.

BACKGROUND OF THE INVENTION

A plurality of different anesthetics are commonly used in combination in modern anesthesia technique. Adjusting the dosages of the individual anesthetics and thus controlling the course of anesthesia is the task of the anesthesiologist. Volatile and intravenously dispensable hypnotics as well as intravenously dispensable opioids are available. Common practice is, furthermore, the combination of volatile and intravenous anesthetics as well as the additional administration of nitrous oxide. The effect of the combined anesthetics does not, as a rule, correspond to the sum of the individual effects of the individual anesthetics, but synergistic interactions occur. This makes the adjusting of the dosages of the individual anesthetics a complex task, which can be supported by a clear graphic representation of the concentration-vs.-effect relationship.

The concentrations of the anesthetics at the site of action (usually the brain) can be calculated by means of so-called pharmacokinetic compartment models from the quantities of said anesthetics fed per unit of time. Based on the concentrations of the active ingredients at the site of action, an effect can be estimated on the basis of common pharmacodynamic interaction models. The interaction of a plurality of anesthetics leads to an anesthesia effect, which can be described as a probability that a defined pain stimulus (e.g., laryngoscopy or skin incision) is tolerated. It is postulated in an article by T. Boullion et al. (Anesthesiology, 2004; 100; 1353-1372) that different combinations of hypnotics and opioids lead to equal anesthesia effects. If the concentration at the site of action is plotted on the y-axis, that of the opioid on the x-axis and the probability that a certain stimulus is suppressed on the z-axis, an effect or response surface is obtained for the probability of the tolerance of a stimulus (e.g., laryngoscopy or skin incision). The contour lines of the response surface, i.e., sections through the response surface in parallel to the x-y plane, yield lines of equal anesthesia effect. These lines of equal effect are called isoboles.

A system for feeding at least one first anesthetic and at least one second anesthetic in a such a way that the quantity being fed is controlled in a quantitatively adjustable manner as well as for displaying the action diagram is described in DE 10 2004 050 717 B3. The x-y coordinate plane with the concentrations of the two anesthetics is shown on the two axes. A response surface determined in advance is superimposed to this coordinate plane, and the chronological sequence of the concentration data of the previous course of anesthesia is displaced as a trajectory in the x-y plane. Furthermore, DE 10 2007 038 975 A1 describes the calculation of an anesthesia effect (NSRI), which expresses the synergistic effect by a numerical value. The NSRI value is constant along isoboles.

The above-described interaction model has been developed for purely intravenous anesthesia, i.e., for a first intravenous anesthetic and a second intravenous anesthetic, and it was later extrapolated to purely volatile anesthesia. New concentration-vs.-effect relationships, which depend on the individual concentrations and the ratios of these concentrations at the site of action, arise in case of balanced anesthesia, in which an intravenously administered hypnotic (e.g., propofol) and volatile anesthetics (a hypnotic, e.g., sevoflurane, and an opioid, e.g., remifentanyl) are used.

SUMMARY OF THE INVENTION

An object of the present invention is to provide a data processing device for an anesthesia device such that the current anesthesia situation can be represented pharmacodynamically correctly and in an easily detectable manner for the anesthesiologist in case of changes in the feed of intravenously administered and volatile hypnotics with simultaneous administration of an opioid. In particular, the transition from an intravenous hypnotic (e.g., propofol) to volatile anesthetics (frequently employed in the induction phase of anesthesia) and vice versa, as well as the balanced administration of an intravenous hypnotic (e.g., propofol) and of a volatile hypnotic and opioids (maintenance phase) will be able to be represented in a better and more easily detectable manner.

According to the invention, a module is provided in the data processing device for pharmacokinetic model calculations, and this module determines and standardizes the respective effective concentration of the anesthetic at the site of action from continuously supplied data on the volume flows of the anesthetics administered, namely, two hypnotics, one of which is an intravenously administered hypnotic and the other a volatile hypnotic, and of an opioid, wherein the concentration of each anesthetic is divided for the standardization by an effect concentration of the same anesthetic determined in advance, at which concentration a preset percentage of patients shows a certain effect. The standardized concentrations of the hypnotics are added up to a total hypnotic concentration. Furthermore, the data processing device is provided with a module for an isobole model calculation, with which calculation at least one isobole is calculated as a curve in a coordinate plane, which is defined by a total hypnotic concentration axis and an opioid concentration axis, wherein the isoboles are calculated in a time-dependent manner as a function of the currently determined standardized concentrations. Examples of effect concentrations are MAC50 and MAC90, which correspond to concentrations of the anesthetic at which 50% and 90% of the patients, respectively, tolerate the "skin incision" stimulus.

Furthermore, the data processing device is provided with a display module, which is set up (configured) to display on the display means a two-dimensional action diagram, in which an indicator of the total hypnotic concentration is plotted on the y-axis and an indicator for the standardized opioid concentration is plotted on the x-axis and in which at least the data of the currently calculated standardized total hypnotic concentration and opioid concentration values and the plurality of the isoboles determined are displayed, the display being adapted to changes occurring in the course of time in the isoboles determined.

In connection with the present invention, the term "module" does not necessarily describe a separate unit in the data processing unit, but it may also be embodied by program parts, which are executed in a processor. If the data processing unit and the modules are described as being set up for something, this comprises especially a corresponding program implementation.

An intravenous hypnotic or opioid is defined in this application as an intravenously administered hypnotic or opioid. A volatile hypnotic is defined as a hypnotic that is administered in the gaseous form via the lungs. The term anesthetic is used in this application as a generic term for hypnotics and opioids.

In a preferred embodiment, the display module is set up to plot the total hypnotic concentration or the concentration in the y-axis and the x-axis, so that the isoboles changing in the course of time are displayed in it as curves with a changing shape and position (mobile isoboles).

The display module is set up in an alternative embodiment to rescale the x-axis and y-axis as a function of the currently determined isoboles in a time-dependent manner such that the position and shape of the isoboles remain unchanged, so that the position of the value pair or value pairs of total hypnotic concentration and opioid concentration being displayed changes in a time-dependent manner.

The display module is set up in a preferred embodiment to store the value pairs determined for the total hypnotic concentration and opioid concentration as a time series and to display them on the display means as a trajectory in the action diagram.

The effect of all active ingredients can be combined by means of the pharmacokinetic interaction models as well as in the knowledge of the respective concentrations of the anesthetics at the site of action, and a combined potency N can be defined, which is obtained from the drug species scaled over the mean efficacy or potency. The combined potency N can be imaged by means of a reversed sigmoid function onto a range from, for example, 0 to 100 or from 0 to 10 or onto a range scaled in a correspondingly different manner (e.g., by means of simple multiplication by a factor or division by that factor). The combined potency can therefore be stated, for example, as NSRI (Noxious Stimulus Response Index):

$$NSRI = 100 \cdot \left(1 - \frac{(N/N')^{sl}}{1 + (N/N')^{sl}}\right)$$

in which N' is a specific N value, at which an NSRI' of 50 is reached, and sl is a slope factor for the transformation of N into NSRI. For further details of the definition and calculation of NSRI, reference is made to DE 10 2007 038 975 A1.

This index NSRI corresponds to the probability of a reaction or response of the patient to a pain stimulus. With the definition of NSRI given above, this equals 100 in an exemplary calculation for an awake patient (i.e., without the use of anesthetic), whereas NSRI tends towards 0 during deep anesthesia (i.e., high concentrations of anesthetics).

According to the present invention, the calculation of NRSI is continuously adapted to the anesthetic concentrations at the site of action. From this arises an NSRI scale that is independent from the ratio of the concentration of the intravenous hypnotic and the concentration of the volatile hypnotic and of the opioid at the site of action, i.e., the probability that a defined pain stimulus is suppressed always corresponds to the NSRI value regardless of the hypnotic selected.

The present invention will be described below on the basis of an exemplary embodiment in connection with the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
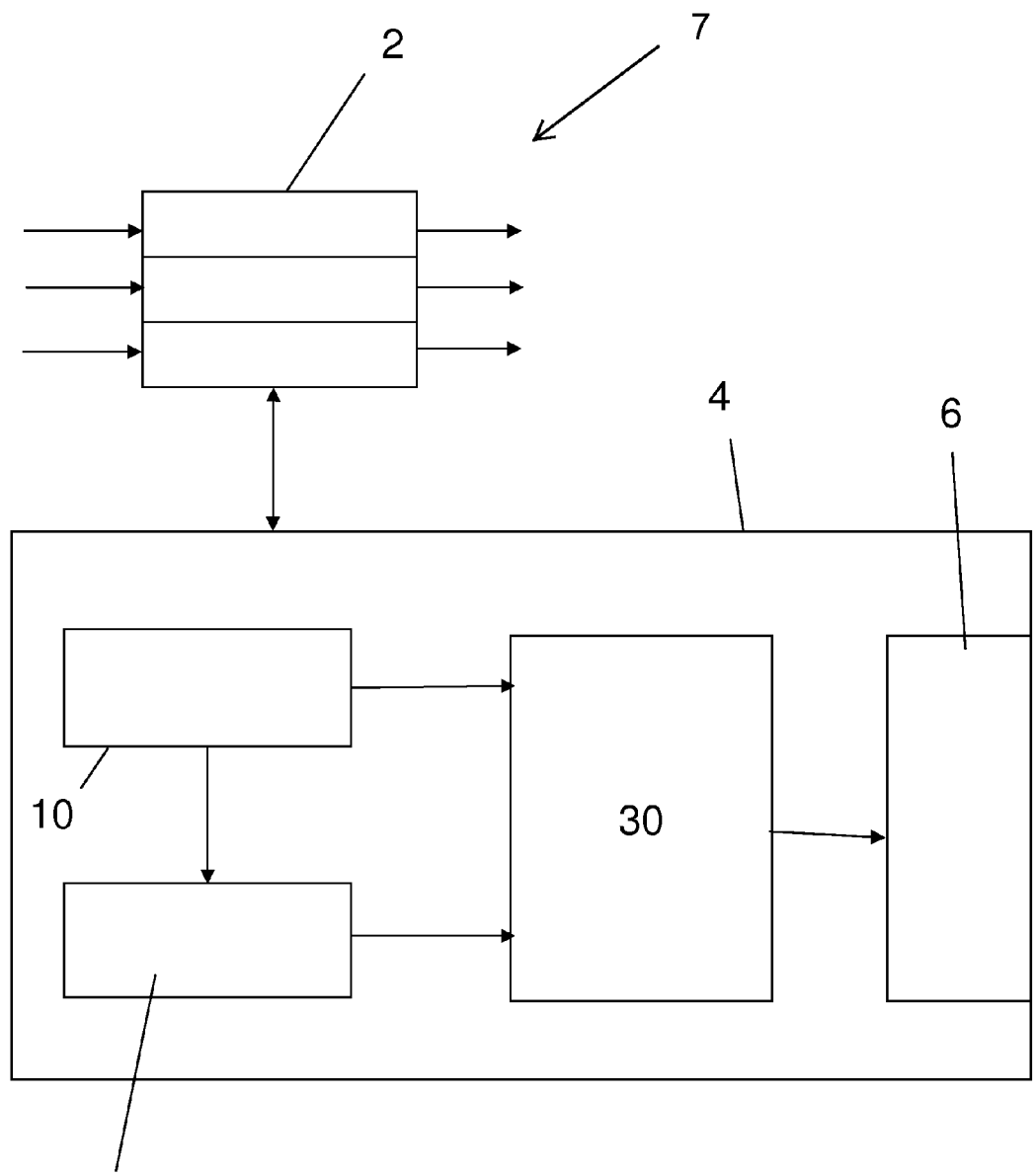
FIG. 1 is a schematic block diagram for a data processing device according to the present invention in an anesthesia device.

Referring to the drawings in particular, FIG. 1 shows a schematic block diagram of a data processing device 4 according to the present invention in an anesthesia device 7. The anesthesia device 7 has three feeding means 2 for feeding three anesthetics, which feeding means 2 are controlled by the data processing device 4 according to the settings performed by the anesthesiologist, in such a way that the feeding is controlled such that the volume can be adjusted. The data processing device 4 comprises a module 10 for pharmacokinetic model calculations, which determines and standardizes the respective effective concentration of the anesthetics at the site of action with the data of the volume flows of the anesthetics from the feeding means 2. For standardization, the concentration of each anesthetic is divided by an effect concentration of that anesthetic, determined in advance, at which a preset percentage of patients shows a certain effect. Furthermore, the standardized concentrations of the hypnotics are combined into a total hypnotic concentration in module 10.

The data processing device 4 comprises, furthermore, a module 20 for an isobole model calculation, in which a plurality of isoboles are calculated as curves in a coordinate plane, which is defined by a total hypnotic concentration axis and an opioid concentration axis, as a function of the currently determined standardized concentrations.

Furthermore, there is a display module 30, which receives the output values from module 10 for pharmacokinetic model calculations and from module 20 for isobole model calculations. An action diagram, in which the y-axis is an indicator of the total hypnotic concentration and the x-axis is an indicator of the standardized opioid concentration, is generated in display module 30. Display module 30 sends the action diagram to the display means 6 in order to display the isoboles in the action diagram. Furthermore, at least the current value pair for the total hypnotic concentration and standardized opioid concentration is sent to the display means 6 and displayed there. The value pairs of the total hypnotic concentration and opioid concentration values determined are preferably stored as a time series and displayed on the display means, so that the course of anesthesia over time is represented as a trajectory in the action diagram.

The connection between the isoboles for an anesthesia with purely intravenous hypnotic and the isoboles for an anesthesia with purely volatile hypnotic is established in the following exemplary embodiment by the assumption that the effect parameter MAC50 for a volatile hypnotic (necessary alveolar concentration for volatile anesthetics to suppress the pain stimulus in response to a skin incision in 50% of patients) is clinically equivalent to the effect parameter TOL50 for an intravenous hypnotic, here propofol (necessary propofol concentrations in the brain to suppress the pain stimulus in response to laryngoscopy in 50% of patients). This means that the pain stimulus in response to skin incision is equated with the pain stimulus occurring during laryngoscopy; this hypothesis is confirmed by a clinical study.

The subscripts "opi" will hereinafter be used in reference to an opioid, "hyp" in reference to a hypnotic, "Vol" in reference to a volatile hypnotic, and "Prop" in reference to propofol as an intravenously administered hypnotic.

The following designations will be used in the following exemplary embodiment:

| Name | Term | Explanation |
|---|---|---|
| TOL | "Tolerance of Laryngoscopy" | Clinical stimulus defined for propofol |
| TOL50, TOL90 | | Anesthesia level at which 50% and 90% of patients, respectively, tolerate the "laryngoscopy" stimulus. |
| TOSS | "Tolerance of Shake and Shout" | Clinical stimulus defined for propofol |
| TOSS50, TOSS90 | | Anesthesia level at which 50% and 90% of patients, respectively, tolerate the "Shake and Shout" stimulus. |
| MAC | "Minimal alveolar concentration" in case of skin incision | Clinical stimulus defined for volatile anesthetics |
| MAC50, MAC90 | | Anesthesia level at which 50% and 90% of patients, respectively, tolerate the "skin incision" stimulus. |
| $P_{tol}$ | Probability | Value range of 0 . . . 1 (0 . . . 100%) |
| $arousal_{in}$ | Numerical value for a defined clinical stimulus | The numerical value has been determined by studies. Different value ranges apply to volatile anesthetics and to propofol. |
| NOS | "Non Opioid suppressible Stimulus" | Percentage of clinical stimulus that cannot be suppressed by the administration of opioids. |
| h | "Steepness" | Steepness of the rise of the response surface. This is a property of the drug. |
| $C50_{opi}$ | | Opioid concentration in the effect organ (site of action) at which 50% of the maximum drug effect is reached. |
| $C50_{hyp}$, $C50_{Prop}$, $C50_{Vol}$ | | Drug concentration of a hypnotic (hyp) in general or of propofol (Prop) or of volatile anesthetics (Vol) in the effect organ (site of action), at which 50% of patients tolerate the "Shake and Shout" stimulus. |
| NSRI | "Noxious Stimulus Response Index" | Index of the probability that a pain stimulus can be suppressed. One NSRI value is exactly assigned to each isobole. |
| sl | "Slope" | Steepness of the rise of the NSRI surface. This is a fixed value. |
| N' | | Reference value for the calculation of NSRI. This is a fixed value. |

The following isoboles are calculated and displayed:

| | Propofol | | | Volatile anesthetics | |
|---|---|---|---|---|---|
| TOL90 | $P_{tol} = 0.9$, $arousal_{in} = 2.83$ | clinically equivalent | MAC90 | $P_{tol} = 0.9$, $arousal_{in} = 1.26$ | |
| TOL50 | $P_{tol} = 0.5$, $arousal_{in} = 2.83$ | clinically equivalent | MAC50 | $P_{tol} = 0.5$, $arousal_{in} = 1.26$ | |
| TOL20 (TOSS90) | $P_{tol} = 0.2$, $arousal_{in} = 2.83$ | clinically equivalent | MAC20 (TOSS90) | $P_{tol} = 0.2$, $arousal_{in} = 1.26$ | |
| TOL02 (TOSS50) | $P_{tol} = 0.025$, $arousal_{in} = 2.83$ | clinically equivalent | MAC02 (TOSS50) | $P_{tol} = 0.025$, $arousal_{in} = 1.26$ | |

$$\frac{C_{hyp}}{C50_{hyp}}(C_{opi}) =$$

$$\left(arousal_{in} - arousal_{in} \cdot (1-NOS) \cdot \frac{\left(\frac{C_{opi}}{c50_{opi}}\right)}{1+\left(\frac{C_{opi}}{c50_{opi}}\right)}\right) \cdot \left(\frac{P_{tol}}{1-P_{tol}}\right)^{\frac{1}{h}}$$

Double subscripts are used if a distinction is made between propofol or volatile anesthetics.

| Name | Explanation |
|---|---|
| $C50_{opi\_Vol}$ | C50 concentration of the opioid in the simultaneous presence of volatile anesthetics only |
| $C50_{opi\_Prop}$ | C50 concentration of the opioid in the simultaneous presence of Propofol only |

The parameters $arousal_{in}$, NOS, $C50_{opi}$, h, which are different for propofol and volatile anesthetics, are weighted with the weighting factor "Fraction" corresponding to the ratio of propofol concentration ($C_{Prop}$) to the concentration of the volatile anesthetic ($C_{Vol}$) at the site of action:

$$Fraction = \frac{\frac{C_{Vol}}{C50_{Vol}}}{\frac{C_{Vol}}{C50_{Vol}} + \frac{C_{Prop}}{C50_{prop}}}$$

The concrete numerical values shown below are used for illustration. They correspond to the current state of knowledge and originate from publications of different clinical studies.

| | | Propofol (_Prop) | Volatile anesthetics (_Vol) |
|---|---|---|---|
| $arousal_{in}$ for TOSS | $arousal_{in}$ = 1 | 1.00 (reference) | 1.00 (reference) |
| $arousal_{in}$ for TOL/ MAC | $arousal_{in}$ = Fraction · $arousal_{in\_Vol}$ + (1 − Fraction) · $arousal_{in\_Prop}$ | 2.83 | 1.26 |
| h | h = Fraction · $h_{Vol}$ + (1 − Fraction) · $h_{Prop}$ | 3.46 | 8 |
| NOS | NOS = Fraction · $NOS_{Vol}$ | 0 | 0.1 |
| $C50_{opi}$ (e.g., remifentanil) | $C50_{opi}$ = Fraction · $C50_{opi\_Vol}$ + (1 − Fraction) · $C50_{opi\_Prop}$ | 1.16 ng/mL | 1.37 ng/mL |
| $C50_{hyp}$ | | 2.99 µg/mL | 1.47 vol. % (e.g., sevoflurane) |

NSRI Equation:

$$NSRI = \frac{100}{1+\left(\frac{arousal_{in}}{N'} \cdot \left(\frac{P_{tol}}{1-P_{tol}}\right)^{\frac{1}{h}}\right)^{sl}}$$

The parameters N', sl are weighted corresponding to the ratio of the propofol concentration and the concentration of the volatile anesthetic at the site of action.

| | | Propofol | Volatile anesthetic |
|---|---|---|---|
| N' | N' = Fraction · $N'_{Vol}$ + (1 − Fraction) · $N'_{Prop}$ | 2.83 | 1.26 |
| sl | sl = Fraction · $sl_{Vol}$ + (1 − $Fraction_{Vol}$) · $sl_{Prop}$ | 2.18 | 5.04 |

The following values are obtained for the NSRI for the four isoboles that are calculated and displayed:

| End point propofol | End point volatile anesthetic | NSRI |
|---|---|---|
| TOSS50 | TOSS50 | 91 |
| TOSS90 | TOSS90 | 70.5 |
| TOL50 | MAC50 | 50 |
| TOL90 | MAC90 | 20 |

Figure 2:
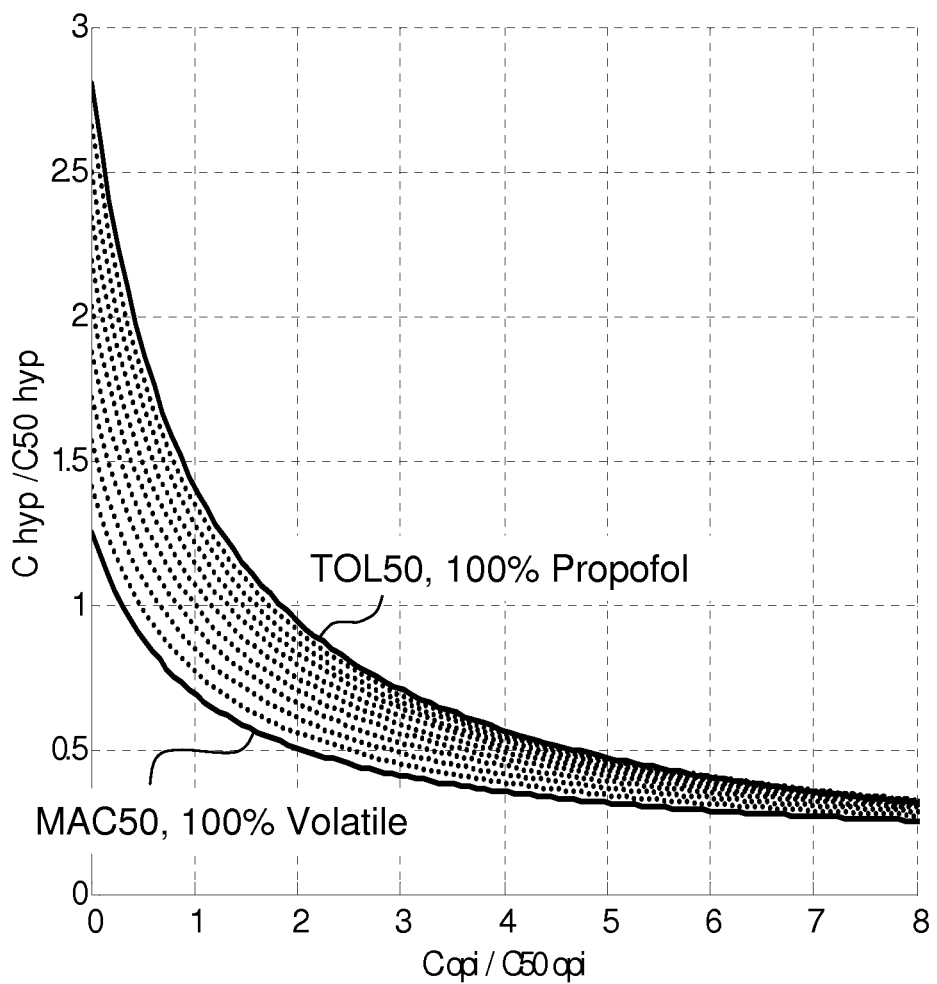
FIG. 2 is an action diagram with an isobole corresponding to TOL50, which illustrates the transition from a purely intravenous hypnotic (100% propofol) to a purely volatile hypnotic (100% volatile) with a plurality of curves corresponding to a plurality of anesthetic mixtures, wherein the standardized total hypnotic concentration $C_{hyp}/C50_{hyp}$ is plotted on the y-axis and the standardized opioid concentration $C_{opi}/C50_{opi}$ on the x-axis.

FIG. 2 shows as an example an action diagram displayed on the display means of the anesthesia device with an isobole corresponding to TOL50 as a family of curves, which is generated at the time of transition from a purely intravenous hypnotic (e.g., 100% propofol) to a purely volatile hypnotic (e.g., 100% sevoflurane). During such a transition from an anesthesia situation with predominantly intravenous hypnotic (propofol) to predominantly volatile hypnotic (sevoflurane), the isobole being displayed on the display means moves through the range defined by the family of curves between an extreme isobole TOL50 for 100% propofol and an extreme isobole MAC50 for 100% volatile anesthetics, e.g., sevoflurane.

Figure 3:
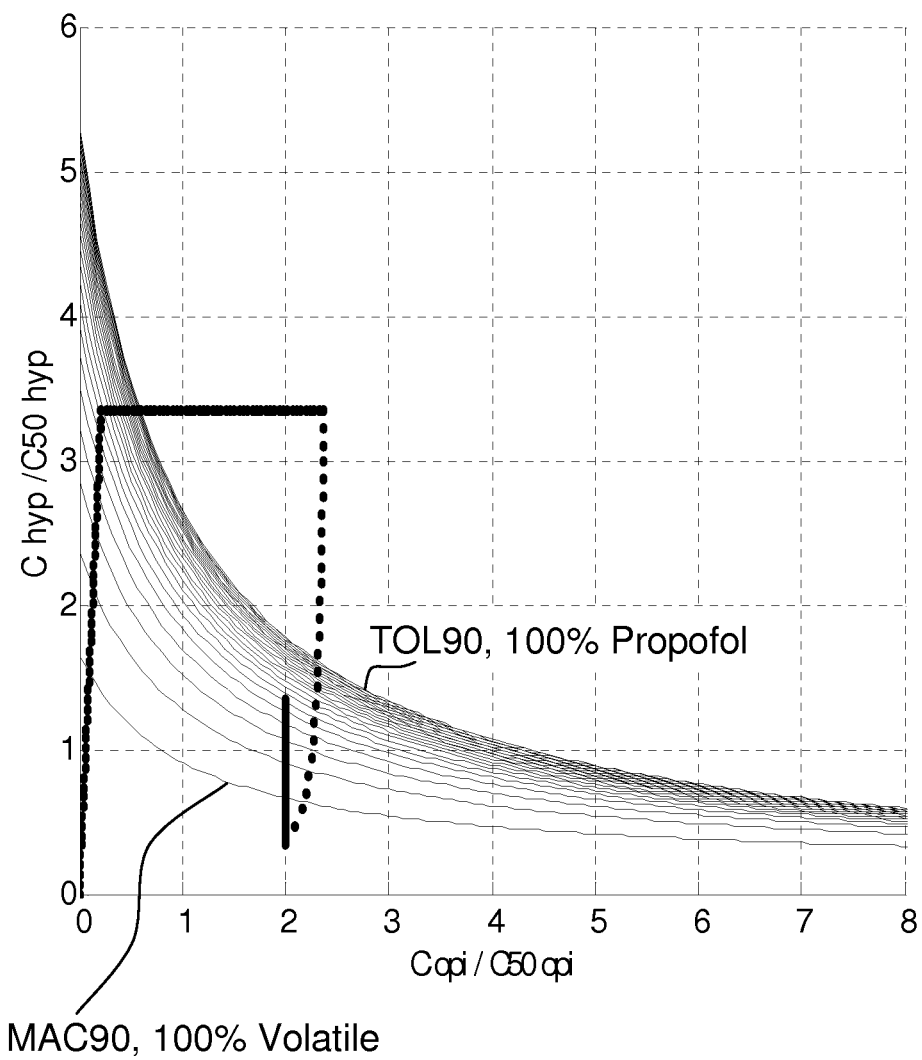
FIG. 3 is an action diagram with an isobole corresponding to TOL90, wherein, as in FIG. 2, the transition from a purely intravenous hypnotic to a purely volatile hypnotic is again shown as a family of curves for the isobole, and the course of anesthesia over time is also shown by dots as a trajectory in the action diagram.

FIG. 3 shows an action diagram with an isobole (as an example for TOL90), which is, in turn, represented as a family of curves, which is obtained during the transition from an extreme isobole TOL90 in case of purely intravenous administration of a hypnotic to an extreme isobole MAC90 in case of purely volatile administration of a hypnotic. Furthermore, the value pairs of the current total hypnotic concentration and opioid concentration are stored in this embodiment as a time series, and the sequence of value pairs is displayed by dots in the action diagram, which together represent the course of anesthesia as a trajectory. Only the isobole corresponding to the currently occurring ratio of intravenous hypnotic to volatile hypnotic is displayed at any time from the family of curves during the time-resolved representation of the value pairs.

Figure 4:
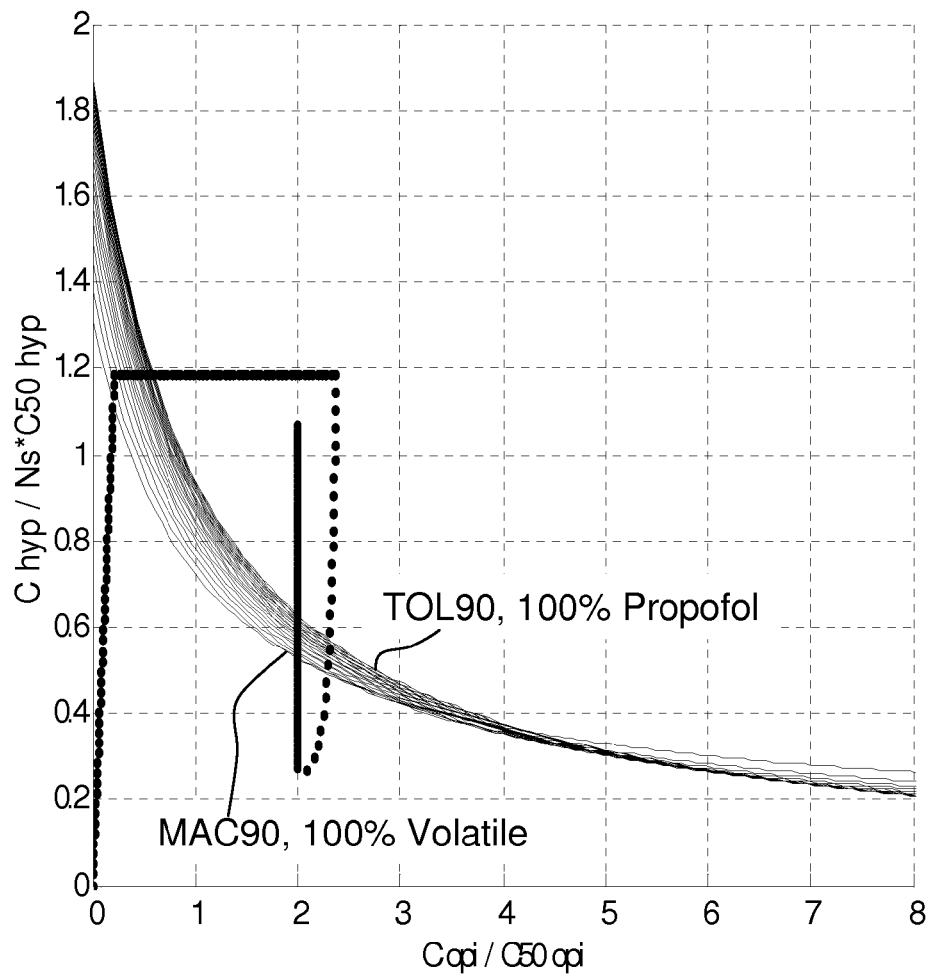
FIG. 4 is a corresponding action diagram as in FIG. 3, wherein the standardized total hypnotic concentration plotted on the y-axis is rescaled such that the change in the position of the isobole is reduced as a function of the relative percentages of intravenous and volatile hypnotic compared to the action diagram in FIG. 3.

FIG. 4 shows an action diagram corresponding to that in FIG. 3, which is obtained during the transition from a purely intravenous hypnotic to a purely volatile hypnotic. The course of anesthesia is also displayed again as a trajectory in the action diagram. Unlike in FIG. 3, the y-axis with the total hypnotic concentration Ns is rescaled here such that the families of curves for the isoboles are in a narrower range, i.e., the isobole is moving less intensively in the action diagram during the transition from a purely intravenous hypnotic to a purely intravenous hypnotic. Only the isobole corresponding to the currently occurring ratio of intravenous hypnotic to volatile hypnotic is displayed at any time from the family of curves during the time-resolved representation of the value pairs.

Figure 5:
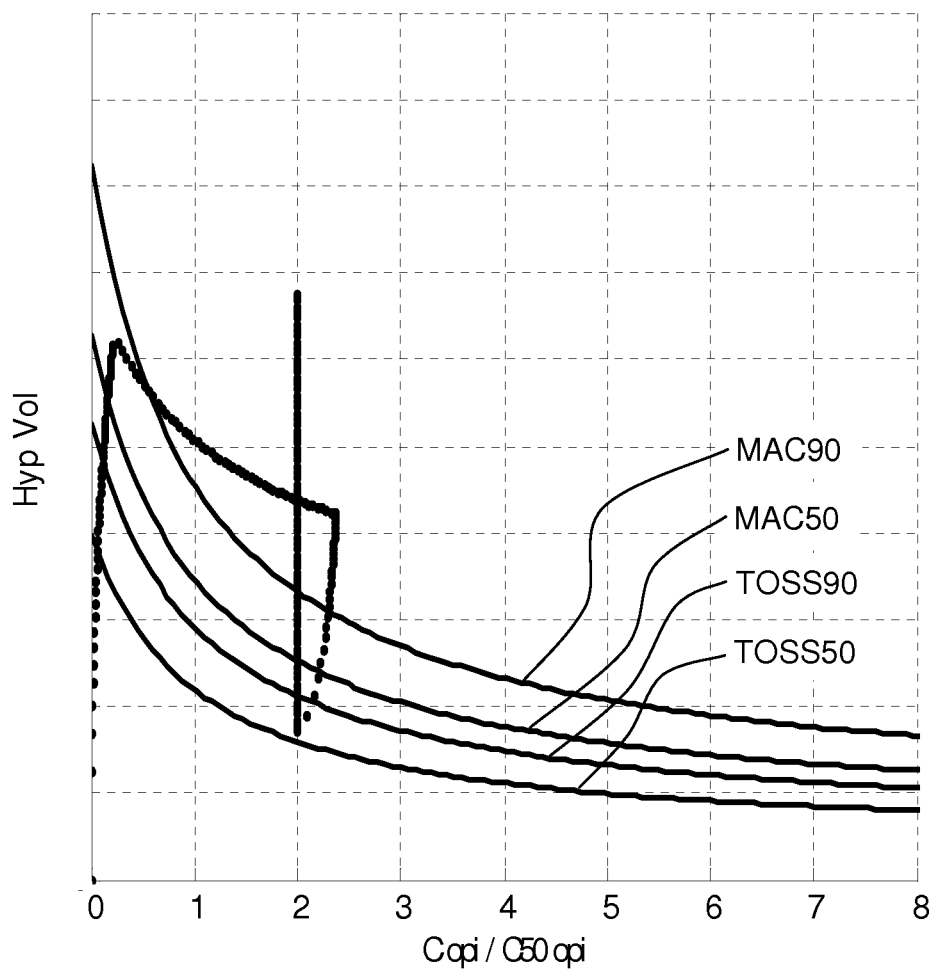
FIG. 5 is an action diagram with four volatile isoboles (MAC90, MAC50, TOSS90 and TOSS50), wherein the standardized total hypnotic concentration is rescaled continuously on the y-axis such that the isoboles remain unchanged during the transition from the purely intravenous hypnotic to the purely volatile hypnotic, while the trajectory showing the course of anesthesia is changed by the rescaling.

FIG. 5 shows an action diagram with four volatile isoboles MAC90, MAC50, TOSS90 and TOSS50, but the y-axis, which is an indicator of the total hypnotic concentration, is rescaled here continuously, corresponding to the ratio of volatile hypnotic to intravenous hypnotic (e.g., propofol), such that the isoboles remain unchanged in this action diagram during the transition from a purely intravenous hypnotic to a purely volatile hypnotic, i.e., families of curves as shown in FIG. 3 and FIG. 4 always coincide in one isobole. By contrast, the shape of the trajectory describing the course of anesthesia changes compared to FIGS. 3 and 4 in this case, in case of equal value pairs of current total hypnotic concentration and opioid concentration.

The data processing device according to the present invention may be integrated, of course, not only in a data processing device of an anesthesia device, but it may also be designed as a separate computing unit and may be connected to an anesthesia device, for example, by means of wires or in a wireless manner. In particular, the data processing device as a whole may be embodied by program parts of a corresponding design, which run in a processor.

Both a display means of the anesthesia device and a separate display means may be used as a display means. For example, the data processing unit according to the present invention and the display means may be integrated in a single device. This device may either be part of an anesthesia device or it may be able to be connected to an anesthesia device as a separate device by means of wires or in a wireless manner.

While specific embodiments of the invention have been shown and described in detail to illustrate the application of the principles of the invention, it will be understood that the invention may be embodied otherwise without departing from such principles.

LIST OF REFERENCE NUMBERS

2 Means for controlled anesthetic feed
4 Data processing unit
6 Display means
10 Module for pharmacokinetic model calculations
20 Module for isobole model calculations
30 Display module for an action diagram
TOL50 Isobole for which 50% of patients tolerate the "laryngoscopy" stimulus
MAC50 Isobole for which 50% of patients tolerate the "skin incision" stimulus
TOL90 Isobole for which 90% of patients tolerate the "laryngoscopy" stimulus
MAC90 Isobole for which 90% of patients tolerate the "skin incision" stimulus
TOSS50 Isobole for which 50% of patients tolerate the "Shake and Shout" stimulus
TOSS90 Isobole for which 90% of patients tolerate the "Shake and Shout" stimulus

What is claimed is:

1. A data processing device for an anesthesia device, which has a feed for three anesthetics including two hypnotics, one of which is an intravenously administered hypnotic and the other a volatile hypnotic, and an opioid, and includes a feed control for adjusting a volume flow, the data processing device comprising:
a data input receiving data of the anesthetic volume flows being fed;
a pharmacokinetic model calculations module to determine and standardize respective effective plasma or site of action concentrations of the anesthetics being administered from continuously fed data of the volume flows of the anesthetics being administered, wherein the determined effective plasma or site of action concentration of each anesthetic is divided for standardization by an effect concentration of the anesthetic, determined in advance, at which a preset percentage of patients shows a certain effect, and the standardized concentrations of the hypnotics are added up to a total hypnotic concentration and provided as pharmacokinetic model calculations module output values;
an isobole model calculation module receiving data, related to currently determined standardized concentrations, from the pharmacokinetic model calculations module and calculating, and providing as isobole model calculation module output values, at least one isobole as an isobole curve in a coordinate plane, which is defined by a total hypnotic concentration axis and an opioid concentration axis, as a function of the currently determined standardized concentrations; and
a display module connected to a display device, the display module receiving pharmacokinetic model calculations module output values and isobole model calculation module output values and forming a two-dimensional action diagram, in which the y-axis is an indicator of the total hypnotic concentration and the x-axis is an indicator of the standardized opioid concentration and in which at least the data of the currently calculated standardized total hypnotic concentration and opioid concentration values are displayed and the at least one calculated isobole curve is displayed, wherein the display is adapted to changes occurring in the at least one calculated isobole curve in the course of time with the standardized total hypnotic concentration and opioid concentration changing in the course of time.

2. A data processing device in accordance with claim 1, wherein the display module forms the action diagram with the total hypnotic concentration and the opioid concentration on the y-axis and x-axis, so that the changes in the at least one isoboles curve in the course of time are displayed with changing curve shape and position.

3. A data processing device in accordance with claim 1, wherein the display module displays changes in the at least one isobole curve in the course of time by rescaling the x- and y-axes as a function of the currently calculated isobole in a time-dependent manner such that the position and shape of the isoboles remain unchanged, so that the position of a value pair of total hypnotic concentration and opioid concentration changes in a time-dependent manner.

4. A data processing device in accordance with claim 1, wherein the display module stores value pairs determined for the total hypnotic concentration and opioid concentration as a time series and provides a display output comprising the value pairs as a trajectory in the action diagram.

5. An anesthesia device comprising:
an anesthetic feed feeding three anesthetics including two hypnotics, one of which is an intravenously administered hypnotic and the other a volatile hypnotic, and feeding an opioid, in such a manner that the feeding is controlled such that the volume flow can be adjusted;
a display device; and
a data processing device comprising:
a data input receiving data of the anesthetic volume flows being fed;
a pharmacokinetic model calculations module to determine and standardize respective effective plasma or site of action concentrations of the anesthetics being administered from continuously fed data of the volume flows of the anesthetics being administered, wherein the determined effective plasma or site of action concentration of each anesthetic is divided for standardization by an effect concentration of the anesthetic, determined in advance, at which a preset percentage of patients shows a certain effect, and the standardized concentrations of the hypnotics are added up to a total hypnotic concentration and provided as pharmacokinetic model calculations module output values;

a isobole model calculation module receiving data, related to currently determined standardized concentrations, from the pharmacokinetic model calculations module and calculating, and providing as isobole model calculation module output values, at least one isobole as a curve in a coordinate plane, which is defined by a total hypnotic concentration axis and an opioid concentration axis, as a function of the currently determined standardized concentrations; and a display module connected to the display device, the display module receiving pharmacokinetic model calculations module output values and isobole model calculation module output values and forming a two-dimensional action diagram, in which the y-axis is an indicator of the total hypnotic concentration and the x-axis is an indicator of the standardized opioid concentration and in which at least the data of the currently calculated standardized total hypnotic concentration and opioid concentration values are displayed and the at least one calculated isobole curve is displayed, wherein the display is adapted to changes occurring in the isobole calculated curve in the course of time with the standardized total hypnotic concentration and opioid concentration changing in the course of time.

6. An anesthesia device in accordance with claim 5, wherein the display module forms the action diagram with the total hypnotic concentration and the opioid concentration on the y-axis and x-axis, so that the changes in the at least one isobole curve in the course of time are displayed with changing curve shape and position.

7. An anesthesia device in accordance with claim 5, wherein the display module displays changes in the at least one isobole curve in the course of time by rescaling the x- and y-axes as a function of the currently calculated isobole in a time-dependent manner such that the position and shape of the isoboles remain unchanged, so that the position of a value pair of total hypnotic concentration and opioid concentration changes in a time-dependent manner.

8. An anesthesia device in accordance with claim 5, wherein the display module stores value pairs determined for the total hypnotic concentration and opioid concentration as a time series and provides a display output comprising the value pairs as a trajectory in the action diagram.

9. A display device comprising:
a display; and
a data processing device comprising:
  a data input receiving data of anesthetic volume flows being fed;
  a pharmacokinetic model calculations module to determine and standardize respective effective plasma or site of action concentrations of the anesthetics being fed from continuously fed data of the volume flows of the anesthetics being fed, wherein the determined effective plasma or site of action concentration of each anesthetic is divided for standardization by an effect concentration of the anesthetic, determined in advance, at which a preset percentage of patients shows a certain effect, and the standardized concentrations of the hypnotics are added up to a total hypnotic concentration and provided as pharmacokinetic model calculations module output values;
  a isobole model calculation module receiving data, related to currently determined standardized concentrations, from the pharmacokinetic model calculations module and calculating, and providing as isobole model calculation module output values at least one isobole as a curve in a coordinate plane, which is defined by a total hypnotic concentration axis and an opioid concentration axis, as a function of the currently determined standardized concentrations; and
  a display module connected to the display, the display module receiving pharmacokinetic model calculations module output values and isobole model calculation module output values and forming a two-dimensional action diagram, in which the y-axis is an indicator of the total hypnotic concentration and the x-axis is an indicator of the standardized opioid concentration and in which at least the data of the currently calculated standardized total hypnotic concentration and opioid concentration values are displayed and the at least one calculated isobole curve is displayed, wherein the display is adapted to changes occurring in the at least one calculated isobole curve in the course of time with the standardized total hypnotic concentration and opioid concentration changing in the course of time.

10. A display device in accordance with claim 9, wherein the display module forms the action diagram with the total hypnotic concentration and the opioid concentration on the y-axis and x-axis, so that the changes in the at least one isobole curve in the course of time are displayed with changing curve shape and position.

11. A display device in accordance with claim 9, wherein the display module displays changes in the at least one isobole curve in the course of time by rescaling the x- and y-axes as a function of the currently calculated isobole in a time-dependent manner such that the position and shape of the isoboles remain unchanged, so that the position of a value pair of total hypnotic concentration and opioid concentration changes in a time-dependent manner.

12. A display device in accordance with claim 9, wherein the display module stores value pairs determined for the total hypnotic concentration and opioid concentration as a time series and provides a display output comprising the value pairs as a trajectory in the action diagram.

13. A data processing device in accordance with claim 1, wherein the display module forming the two-dimensional action diagram includes forming a display signal output which changes in time, corresponding to changes occurring in the at least one calculated isobole based on changes in the standardized concentrations relating to changes in the ratio of the two hypnotics and changes in value pairs determined for the total hypnotic concentration and opioid concentration.

14. A data processing device in accordance with claim 13, further comprising a display receiving the display signal output and displaying the calculated isobole with the display adapting to changes occurring in the at least one calculated isobole and with the display adapting to changes occurring in value pairs determined for the total hypnotic concentration and opioid concentration.

15. An anesthesia device in accordance with claim 5, wherein the display module forming the two-dimensional action diagram includes forming a display module output which changes in time, corresponding to changes occurring in the at least one calculated isobole based on changes in the standardized concentrations relating to changes in the ratio of the two hypnotics and changes in value pairs determined for the total hypnotic concentration and opioid concentration.

16. An anesthesia device in accordance with claim 15, further comprising a display receiving the display module output and displaying the calculated isobole with the display adapting to changes occurring in the at least one calculated isobole and with the display adapting to changes occurring in value pairs determined for the total hypnotic concentration and opioid concentration.

17. A display device in accordance with claim 9, wherein the display module forming the two-dimensional action diagram includes forming a display signal output which changes in time, corresponding to changes occurring in the at least one calculated isobole based on changes in the standardized concentrations relating to changes in the ratio of the two hypnotics and changes in value pairs determined for the total hypnotic concentration and opioid concentration.

18. A display device in accordance with claim 17, wherein the display receives the display signal output and displays the calculated isobole with the display adapting to changes occurring in the at least one calculated isobole and with the display adapting to changes occurring in value pairs determined for the total hypnotic concentration and opioid concentration.

* * * * *